United States Patent [19]

Bruno

[11] Patent Number: 4,826,073

[45] Date of Patent: * May 2, 1989

[54] CONTAINER FOR STORAGE AND DISPOSAL OF POTENTIALLY INJURIOUS IMPLEMENTS SUCH AS USED SCALPEL BLADES, HYPODERMIC NEEDLES AND THE LIKE

[76] Inventor: John Bruno, 3015 South Ocean Blvd., Highland Beach, Fla. 33431

[*] Notice: The portion of the term of this patent subsequent to Feb. 2, 2005 has been disclaimed.

[21] Appl. No.: 112,969

[22] Filed: Oct. 23, 1987

Related U.S. Application Data

[60] Division of Ser. No. 869,845, May 28, 1986, Pat. No. 4,722,470, Continuation of Ser. No. 513,616, Jul. 14, 1983.

[51] Int. Cl.⁴ .......................... B65D 5/10; B65D 85/00
[52] U.S. Cl. .................................... 229/128; 229/124; 229/907; 229/104; 229/183; 229/185; 206/366; 206/370; 206/491
[58] Field of Search ............... 229/128, 124, 907, 104, 229/183, 185; 206/366, 367, 370, 491, 363

[56] References Cited

U.S. PATENT DOCUMENTS

| | | | |
|---|---|---|---|
| 1,713,631 | 5/1929 | Tinsley | 229/37 E |
| 3,746,155 | 7/1973 | Seeley | 206/365 |
| 3,946,937 | 3/1976 | Forbes, Jr. et al. | 229/37 E |
| 4,121,755 | 10/1978 | Meseke et al. | 206/366 |
| 4,315,592 | 2/1982 | Smith. | |
| 4,375,849 | 3/1983 | Hanifi. | |
| 4,452,358 | 6/1984 | Simpson. | |
| 4,453,648 | 6/1984 | Harris et al. | |

Primary Examiner—Joseph M. Moy

[57] ABSTRACT

A container for safely storing potentially injurious implements such as scalpel blades, hypodermic needles, etc., comprises a plurality of wall panels forming an enclosure. The container includes a top closure panel hingedly attached to one wall panel of the container, the top closure panel extending angularly inwardly into the container toward the opposite wall panel and forming a trough-like receiving chamber with the opposite container wall for initially receiving implements to be stored therein. Stop means are formed on the container for limiting upward angular rotation of the top closure panel to maintain the closure panel at a pre-determined angle. Once received in the trough-like chamber, the implements will drop into the interior of the container by pushing downwardly on the top closure panel.

20 Claims, 3 Drawing Sheets

CONTAINER FOR STORAGE AND DISPOSAL OF POTENTIALLY INJURIOUS IMPLEMENTS SUCH AS USED SCALPEL BLADES, HYPODERMIC NEEDLES AND THE LIKE

This is a divisional of co-pending application Ser. No. 869,845 filed May 28, 1986, which, in turn, is a File Wrapper continuation of application Ser. No. 513,616, filed July 14, 1983.

BACKGROUND AND OBJECTS OF THE INVENTION

The present invention relates generally to receptacles, containers and the like, and, more particularly, to containers for safely handling potentially injurious or contaminated implements such as used scalpel blades, hypodermic needles and like devices which pose a risk of causing infection or even disease if an open wound is created by or exposed to such implement.

With the advent of disposable surgical tools, hypodermic needles, scalpel blades and other sharp implements, a need has developed for a receptacle to store such devices after use without risk of exposing people to injury, infection or disease by improper handling, until proper disposal can be made. In fact, the very recent outbreak of the highly contagious AIDS disease has dramatically highlighted the need for a safe way of handling the storage and disposal of such implements.

In the case of disposable hypodermic needles, it is common practice to break or cut the needles prior to discarding in order to reduce the size of the needle/syringe as well as eliminate the sharp point from the needle for reducing the risk of injury from improper handling. Usually, a special tool is used to cut off the needle points and store them in an attached container. In breaking or cutting the needles, however, there is a risk of accidental puncture during the breaking or cutting operation, thus exposing the holder to possible injury and, further, to possible infection or disease. In addition, any residual medication in the needle is susceptible to splattering onto the person or his clothes and there is a danger that potentially harmful fumes could be inhaled. Furthermore, inasmuch as the blades of the cutting tool are seldom, if ever, changed, they become a breeding ground for germs, bacteria and other disease-causing micro-organisms to which the unsuspecting cutter is unnecessarily exposed.

Several proposals have been advanced for avoiding the foregoing dangers. However, although these proposals may eliminate some of the risks involved in the handling and storage of hypodermic needles and the like, they generally do not overcome all of the dangers and often are the source of other problems. For example, at least one manufacturer suggests using the empty shipping containers used for shipping its fresh disposable needles to store and dispose of the needles after use. Although these containers can hold spent needles, they do not provide any margin of safety against the risk of injury from the fully exposed needles because these containers are only intended to safely hold new needles which are already contained in blister-style packaging that inherently protects against injury by the sharp needle points. In addition, because the shipping containers must be large enough to hold new needles and their protective packaging, these containers are larger than needed for storing the used needles and, as a result, are too bulky to fit conveniently on, for example, service carts used in hospitals and like institutions where the concern for storage and disposal of needles is the greatest. Also, since the needles are simply dropped into the box, the sharp needle points become oriented haphazardly in all directions so as to increase the risk of injuring a person and hinder efficient or compact packing of the implements.

A few specially designed containers have been proposed for handling used needles. Known presently available containers include the "SAN-I-PAK" sold by Med-Safe Systems, Inc. of Leucadia, Calif., a cylindrical container sold by Sage Products of Cary, Ill., a cardboard box sold under the designation "HYPO-HOPPER" sold by the Porex Medical Division of Glasrock Medical Services of Fairburn, Ga. and another cardboard box sold as catalog number 5684 by Becton-Dickenson of Rutherford, N.J.

Although the specially designed devices provide adequate results under certain circumstances, they do suffer certain disadvantages. For example, the Med-Safe and Sage devices, being are molded from plastic, can be relatively expensive. Similarly, the Porex device, although made of corrugated paper, has a relatively complicated baffle/lock mechanism which can add to the cost of fabrication and assembly. In addition, both cardboard devices generally have single layer side walls and directly abutting double walled bottoms which do not provide any added margin of safety against possible punctures especially if the bottom becomes wet. Furthermore, in all the containers, either the entire syringe/needle or the syringe with a part of the needle is simply dropped into the containers, thus creating a haphazard distribution of needles in the container which can result in an inefficiently filled container and possible injury to a user.

Accordingly, it is an object of the present invention to provide a new and improved container for storage and/or disposal of hypodermic needles, scalpels and other sharp or pointed implements which pose a danger of injury or puncture (hereinafter referred to simply as "potentially injurious implements"). It is another object of the present invention to provide a new and improved container structure for storing potentially injurious implements, which can be fabricated relatively inexpensively yet is sturdy and resistant to puncture by the implements retained therein.

It is also an object of the present invention to provide a new and improved container structure for storing potentially injurious implements, which can be fabricated from a single sheet of relatively inexpensive material such as corrugated paper, cardboard, stiffened paper and the like. It is a further object of the invention to provide such a container structure which can be shipped and stored in a substantially flat unassembled configuration, yet can be assembled with relative ease and without requiring any bonding or fastening means to complete assembly.

It is still another object of the invention to provide a new and improved container for potentially injurious implements, which is adapted to receive all the implements in a compact side-by-side horizontal configuration for maximum storage capacity. It is also an object of the invention to provide such a container which further includes a biased door adapted to prevent any implements from falling out once stored therein. In addition, it is an object of the invention to provide such a container which can be permanently sealed for final disposal.

It is yet a further object of the present invention to provide a new and improved container for storing potentially injurious implements, which is compact for convenient mounting to a service cart or other device for moving medical treatment supplies.

The foregoing specific objects and advantages of the invention are illustrative of those which can be achieved by the present invention and are not intended to be exhaustive of the possible advantages which can be realized. Thus, these and other objects and advantages of the invention will be apparent from the description herein or can be learned from practicing the invention, both as embodied herein or as modified in view of any variations which may be apparent to those skilled in the art. Accordingly, the present invention resides in the novel parts, constructions, arrangements, combinations and improvements herein shown and described.

SUMMARY OF THE INVENTION

The present invention includes a container for handling used hypodermic needles, scalpels and like potentially injurious implements as well as a sheet-like blank for forming such a container. Briefly described, the container according to the present invention includes a box-like member having front and back wall panels spaced apart by a pair of oppositely disposed side wall panels which are adapted to adjoin opposite edges of the front and back walls. A bottom wall assembly joined at the bottom edge of one of the wall panels is adapted to close the bottom of the box-like member at the bottom edges of the remaining wall panels to form a closed-bottom container having a generally hollow interior to receive discarded implements. A top closure panel is hingedly joined at the top edge of one of the wall panels and is adapted to be folded into the hollow container interior to form a "trap door" closure of the top of the container. As preferably embodied, the top panel and the bottom wall assembly are joined to either the front panel or the back panel.

Advantageously, the top closure panel is adapted to extend angularly inwardly into the hollow interior of the container to form a trough-like receiving chamber for initially receiving implements to be stored in the container. In addition, the top panel advantageously is wider than the depth of the box-like member and is biased in the upward direction so that once pushed into the interior chamber, it automatically returns to its original position to close off the top of the container by abutting the wall panel opposite its hinged connection. An implement can thus be simply released into the trough-like receiving chamber and thence caused to drop into the hollow interior of said container by pushing down on the top closure panel so that the implement simply falls into the container by its own weight without requiring any further handling by a person.

Also as preferably embodied, the bottom wall comprises a double-walled assembly made up of a pair of spaced-apart wall members to help prevent a sharp point or implement from penetrating or puncturing through the bottom wall and risk injuring a person. Advantageously, the box-like member includes a second top panel which can serve as a support for suspending the box-like member in use, if desired, and can serve as an extra closure member for sealing the box-like member once it is filled.

The container structure according to the present invention is preferably made, and can be made, from a sheet of corrugated paper, cardboard or stiffened paper or the like.

It will be readily apparent from the foregoing general description, as well as the following detailed description, that the objects and advantages specifically enumerated herein are achieved by the invention as embodied herein. For example, by providing the enlarged-width top panel member which is hingedly joined to the box-like structure and self-biased to rest adjacent the opposite wall panel, the container is completely closed during use to prevent any inadvertant injury yet it remains available to receive more discarded implements. In addition, the biased top panel provides a "trap door" which, as part of the trough-like receiving chamber, minimizes the amount of potentially injurious contact a person must have with the implements when disposing of them.

By utilizing the spaced double-walled bottom wall assembly, the container provides a significant margin of safety against the possibility that a sharp point or edge might puncture through the bottom wall and be exposed for possibly injuring a person as well as providing protection even though the bottom-most panel becomes wet. In addition, since, as described in detail below, the bottom wall assembly can be friction fit within the bottom of the box-like member, bottom tabs can be provided on the bottom edges of the side wall panels for folding into the interior to enhance the friction fit and also provide at least a partial second side wall panel on each side of the container to protect against any similar puncture through the side walls of the container.

Because the container can be fabricated from a single sheet of material, it can be economically fabricated and, once the wall panels are fully joined together, the container can be shipped in a flattened condition (i.e., with the front wall panel and one side wall panel doubled over the back wall panel and the other side wall panel) and fully assembled at the site of end use without requiring any tape, staples, glue or other fastening or bonding means.

It will also be found that the arrangement of the hinged top closure panel according to the invention prevents any implements from falling out if the container is accidentally inverted. In fact, the weight of the implement against the top panel actually enhance the closure provided by the top panel, thus making the container "dump proof".

It will be appreciated by those skilled in the art that the foregoing brief description and the following detailed description are exemplary and explanatory of the invention but are not intended to be restrictions thereof. Thus, the accompanying drawings, referred to herein and constituting a part hereof, illustrate preferred embodiments of the invention and, together with the detailed description, serve to explain the principles of the invention.

DETAILED DESCRIPTION OF PREFERRED EMBODIMENTS

Figure 1:
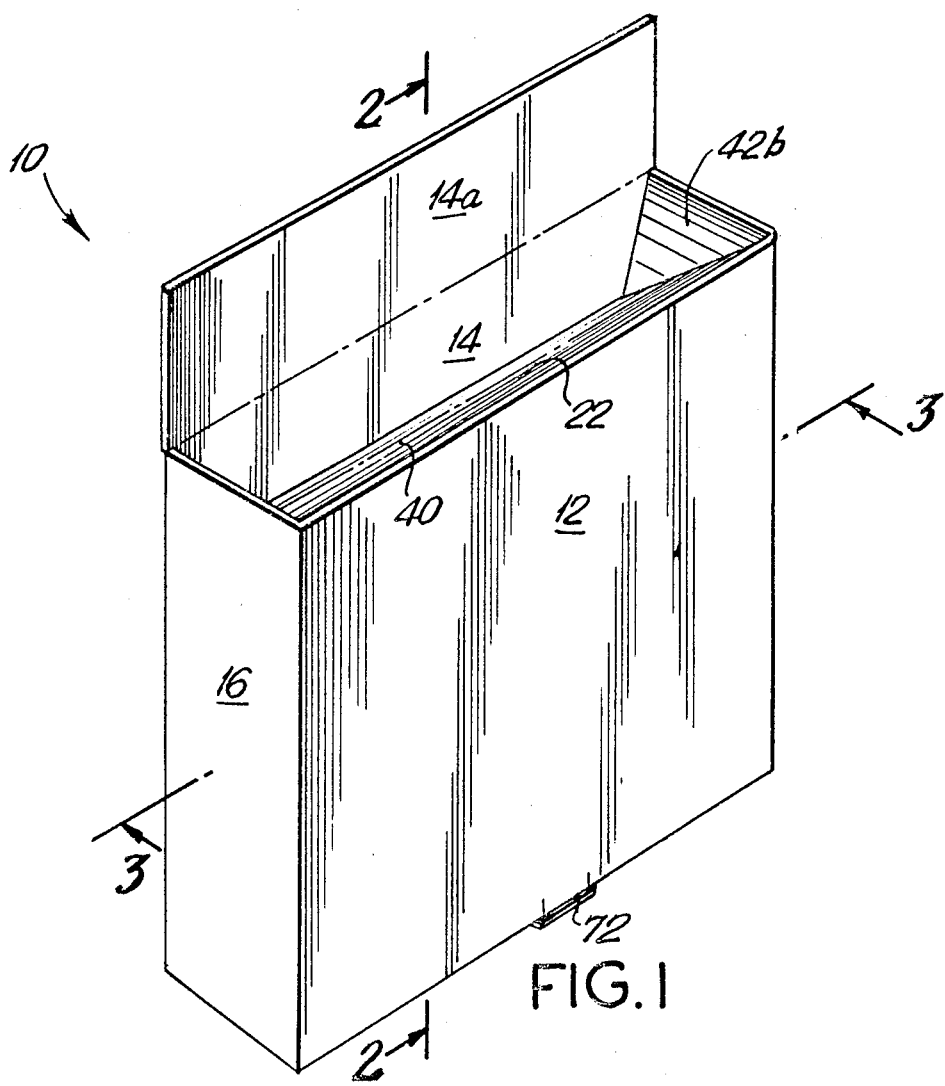
FIG. 1 is an isometric view of an embodiment of a container according to the present invention.

Turning now to the drawings wherein like reference characters refer to like parts throughout the various views, there is shown a container (indicated generally at 10) according to the present invention as well as a cut and scored sheet-like blank for making a container according to the present invention.

Figure 2:
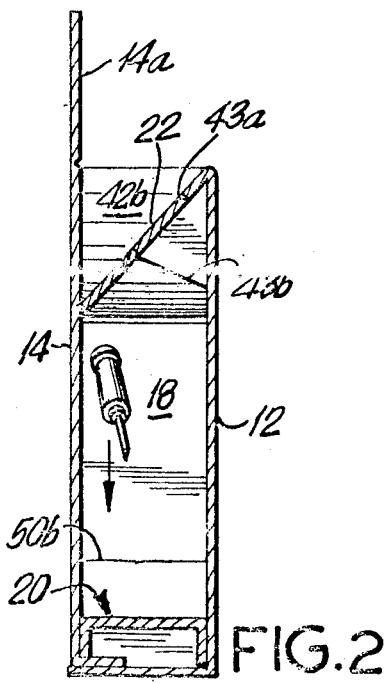
FIG. 2 is a sectional view taken along section lines 2—2 of FIG. 1.
Figure 3:
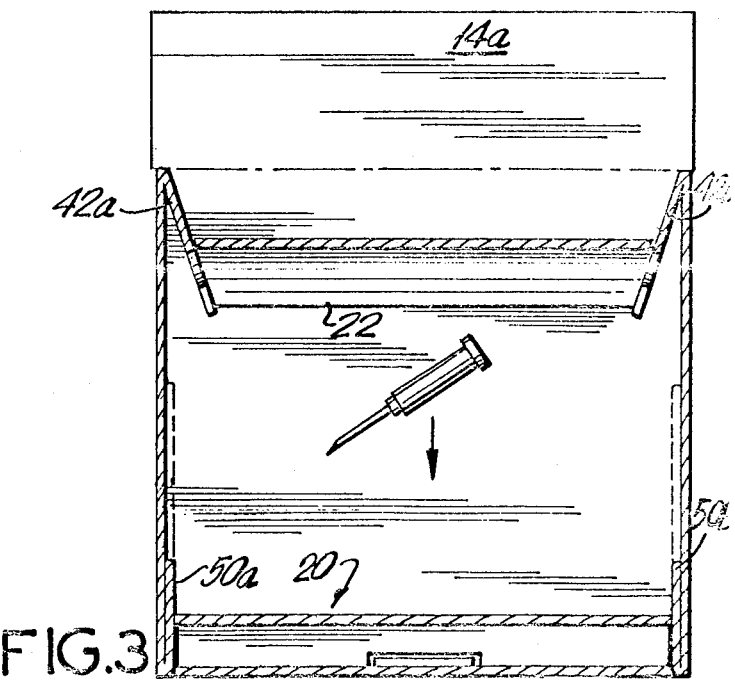
FIG. 3 is a sectional view taken along section lines 3—3 of FIG. 1.

Referring more particularly to FIGS. 1–3, there are shown various views of container 10 according to the present invention. As here embodied, container 10 includes a front wall panel 12, a back wall panel 14 and a pair of oppositely disposed side wall panels, 16 and 18 (18 is not visible in FIG. 1), which maintain the front and back wall panels in spaced apart relation. Bottom wall assembly 20 (preferably a double-walled member as explained in greater detail below) seals off the bottom of container 10 to form an hollow interior chamber for discarded implements.

Container 10 is particularly adapted to receive and safely store such potentially injurious implements as used hypodermic needle assemblies (i.e., the needle and syringe), scalpel blades and like sharp devices which require special care in handling because of not only the risk that the implement may puncture or otherwise injure a person but also the concern that the implement can cause infection or disease because of bacteria, germs or other contaminants it may contain. To this end, the top of container 10 is preferably formed with closure means which can be readily opened for receiving the implement to be discarded, yet will keep the opening closed at all other times to prevent any implements therein from falling out.

As here embodied, flap-like top closure panel 22 is hingedly joined to the top edge of front wall 12 and is adapted to extend angularly into the open box chamber. Advantageously, the width of panel 22 (i.e., the distance from its hinged connection with panel 12 to its inward free end edge, or distal edge) is greater than the corresponding depth of the container (i.e., the distance between the front and back wall panels) so that its inward, or distal, edge is forced to reside within the interior chamber of container 10 at an angle with respect to the top edges of the wall panels. In this way, panel 22 forms a sloped entry guideway to the interior chamber for ensuring that the implements uniformly enter the container in the proper horizontal orientation for storage in side-by-side relation. In addition, panel 22 provides a barrier for preventing implements from falling out of the container once they are deposited therein. Advantageously, the hinged joinder of panel 22 with the top edge of front panel 12 is self-biased so that the distal edge of panel 22 is constantly urged upwardly to maintain closure of the container. It will thus be understood that the material making up the hinged connection should be generally resilient (or could be reinforced with a piece of tape preferably applied before panel 22 is folded into the container) to withstand repeated opening and closing.

Figure 6:
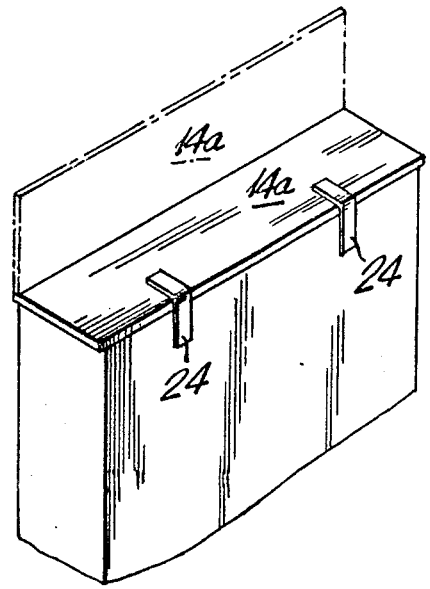
FIG. 6 is a view similar to that shown in FIG. 5 showing the additional top closure panel sealed over the top of the container.

Also advantageously, back wall panel 14 includes an upstanding panel (indicated at 14a) which projects beyond the top edges of the other container walls. Upstanding panel 14a provides both a support means for suspending the container, if desired, from any convenient location, as well as an additional closure member for sealing the container once it is filled. The latter can be carried out simply by folding panel 14a down onto the top edges of the other wall panels and securing it in a closed configuration as by placing tape segments 24 over panels 14a and 12, as shown in FIG. 6.

Figure 4:
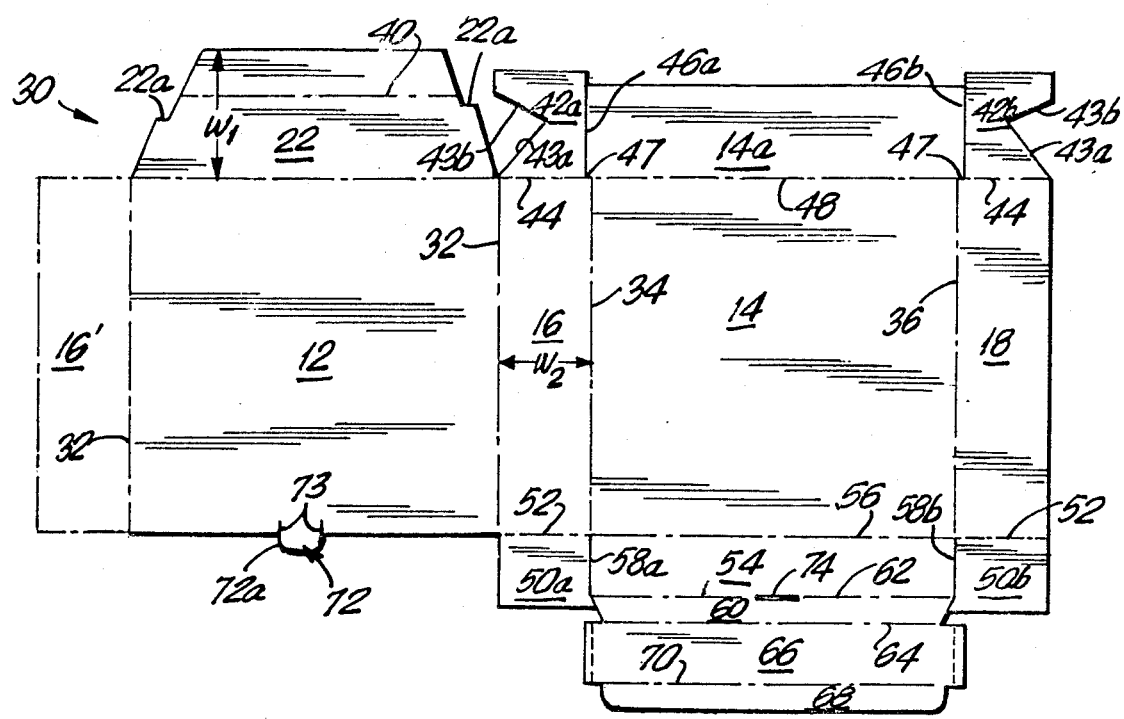
FIG. 4 is a plan view of a sheet-like blank for making a container according to the present invention.

Turning now to FIG. 4, there is shown another aspect of the present invention which serves to illustrate the ease with which container 10 can be fabricated and assembled as well as provide a better understanding of the operation of container 10 when assembled. As shown in FIG. 4, container 10 is advantageously fabricated by appropriately scoring and die-cutting a single sheet of material such as a sheet of corrugated paper (which is considered to be preferred because of its low cost and because of the common use made of such material for boxes, containers, etc.), cardboard, stiffened paper or even certain plastics. Where corrugated paper is used, B-flute grade is preferred. Corrugated plastic may be preferred when the container is to be used near sinks or in other applications where it will be exposed to water or other liquids.

As here embodied, the sheet (indicated generally at 30) used to form container 10 is very generally L-shaped in appearance, with the short leg adapted to form the bottom wall assembly of container 10 and the long leg adapted to form the various wall panels and top panels of the container. In order to form the main wall panels, blank 30 is folded about 90° along a first score line 32 (which extends perpendicular to what become the top and bottom edges of the assembled container) to form front panel 12. The blank is then folded another 90° along a second score line 34 to form one sidewall (here indicated at 16), and it is again folded by 90° along a third score line 36 to form back wall panel 14 and the remaining side wall 18. When so folded, the free edges of walls 18 and 12 will abut each other along their entire lengths to form a corner of the container, and can be joined together by tape (not shown) or any other suitable attachment means. Alternatively, an overlapping side wall panel (indicated in phantom at 16') can be formed along the free edge of front panel 12 by folding the blank along another score line (indicated in phantom at 32'). Panel 16' is simply overlapped onto panel 16, and the two panels are joined together by gluing or otherwise securing them together in any conventional manner. In either form attachment of the wall panels to complete formation of the box-like member can thus be simply and easily accomplished by conventional joinder means which allows the container to be shipped in a collapsed but easily assemblable configuration at the end use site for minimizing the volume occupied by unassembled containers.

Closure panel 22 is provided by a portion of the blank formed along what becomes the top edge of the assembled container and is formed by folding the blank along score line 38 which is essentially coincident with the top edge of the front wall panel. As is best seen in FIG. 4, closure panel 22 tapers towards its free end, with a step-like indentation (indicated at 22a) to facilitate fitting within the slots formed in the top tabs (42a and 42b) as will be explained in further detail below. Since the width ($W_1$) of closure panel 22 is greater than the width ($W_2$) of side panels 16 and 18, panel 22 is advantageously scored at about its midsection, as indicated at 40 (preferably to fold upwardly), to permit it to be folded in order to facilitate insertion, during assembly, into the open chamber of container 10. Panel 22 will thus retain virtually all of its structural integrity to provide the closure function as described above, yet can be easily inserted into the box during assembly without damage.

Both side panels 16 and 18 are formed with identical, but reversed, tab members (indicated at 42a and 42b) which are delineated from the side wall panels by score lines 44 to act as guides for the opening and closing action of closure panel 22. To this end, each tab 42a and 42b is formed with a cut-out or notch (indicated at 43) which forms a stop edge (43a) and a clearance edge (43b) that intersect at an angle of about 75° to about 90° with respect to each other. It will be understood that stop edges 43a define the upward limit of travel for closure panel 22 and should advantageously be proportioned so that the distal edge of panel 22 is at least closely adjacent, or abuts, panel 14 when panel 22 rests against stop edges 43a. Advantageously, each stop edge 43a should preferably form an angle of about 20° to about 60° (preferably 22.5° but up to about 45°) with repect to its adjacent score lines 44 to permit sufficient slant on panel 22 to ensure that implements dropped into the opening will fall to the most recessed portion of the trough formed between panels 22 and 14, so as to be distant from a user's fingers when the panel is pushed inwardly for dropping the implement into the container 10.

It will also be understood that the length of stop edges 43a should be no less than (and, preferably, slightly longer than) the length of the tapered edges of panel 22 between score line 38 and step 22a to ensure that the panel is free to open and close without interference by the tabs 42a and 42b. It will also be understood that since tabs 42a and 42b will tend to turn upwardly, they close any gap which otherwise might exist between the side edges of panel 22 and the side wall panels 16 and 18, (as is evident from FIG. 1) for, e.g., containing fumes, moisture and particles within the container.

It will further be understood that tapered side edges of panel 22 facilitate its swinging movement over side tabs 42a and 42b. In addition, indentation 22a serves to recess the innermost portion of the side edges of panel 22 that actually slide over the tabs so as to reduce the friction generated by the movement of panel 22.

Tabs 42a and 42b may advantageously be formed from a relatively elongated panel member (not numbered) which is an extension of the side wall panels and back wall panel 14 of blank 30. The remaining center portion can thus be used to form additional top closure panel 14a. To this end, tabs 42a and 42b are separated from panel 14a by cut lines 46a and 46b, while panel 14a is delineated from back wall panel 14 by score line 48. Advantageously, each cut line 46a and 46b has a short offsetting segment (both indicated at 47) to form a protruding portion on each end of closure panel 14a which extends slightly beyond the two side wall panels to ensure that the container top is completely closed when the additional top panel 14a is closed down over the top edges of the container.

The bottom edge of each side wall panel may also be formed with a tab (indicated at 50a and 50b) which is delineated by a score line, each indicated at 52. Bottom tabs 50a and 50b are useful in securing the bottom wall assembly when container 10 is fully assembled, as will be described more fully hereinafter. Advantageously, tabs 50a and 50b may be somewhat elongated (as indicated in phantom in FIG. 3) so that when folded into the interior chamber of container 10, they form a double wall along most of the side wall panels 16 and 18 for adding a margin of protection against a puncture through a side wall.

As shown in FIG. 4, the blank for the bottom wall assembly is formed as the short leg of the L-shaped blank along the bottom edge of back wall 14. However, it will be understood that the bottom wall assembly could be formed along the bottom edge of front wall 12.

The bottom wall assembly includes bottom panel member 54 joined to and extending beyond what becomes the bottom edge of back wall panel 14. Panel 54 is delineated by score line 56 which is generally coincident with the bottom edge and by cut lines 58a and 58b which separate it from the two side wall tabs 52. Cut lines 58a and 58b may have offset cut segments (not shown) similar to offset cuts 47 so that the side edges of bottom panel 54 will overlap the bottom edges of side wall panels 16 and 18 to ensure complete closure of the bottom of the container in essentially the same manner as was described above with respect to additional top panel 14a.

Extending beyond bottom panel 54 is a first spacer panel 60 which is delineated from panel 54 by score line 62. Score 62 is separated from score 56 by a distance equal to the width ($W_2$) of side walls 16 and 18 to ensure a snug fit of the bottom wall along the bottom edges of the container. Extending still beyond first spacer panel 60 is interior bottom panel 66 which is delineated by score line 64, and, beyond that, a second spacer panel 68 which is delineated by score line 70. The two intermediate panels 68 and 60 are proportioned so as to provide uniform spacing between panels 54 and 66.

A locking tongue 72 may also formed along the bottom edge of front panel 12 with a projecting tab 72a at its end, for insertion into slot 74 which is formed in and is generally coincident with a portion of score line 62. Tongue 72 provides additional locking to securely hold the bottom wall assembly to the container.

Figure 7:
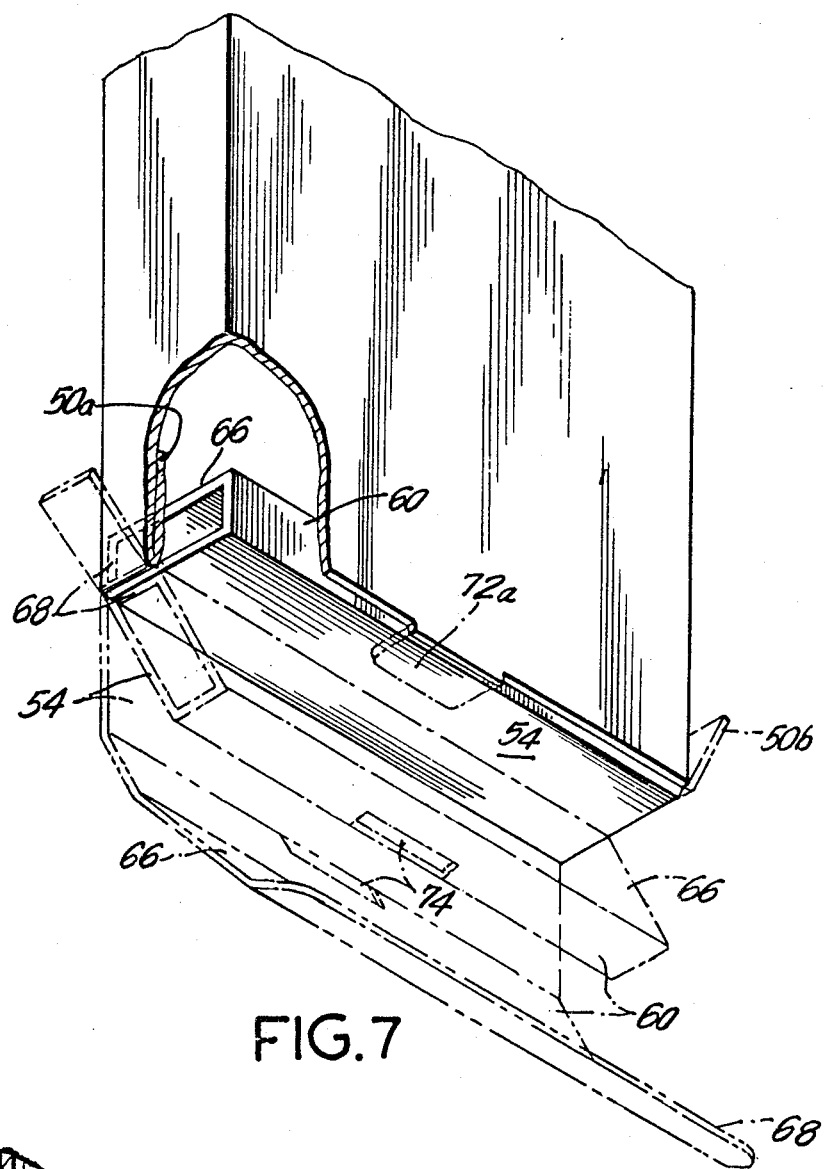
FIG. 7 is an isometric view of the bottom wall assembly of a container according to the present invention, showing the assembly thereof.

Once the basic box-like structure is established as described above, the top and bottom closure assemblies can be assembled. Turning first to the bottom assembly, tabs 50a and 50b are folded into the interior of the container (The small triangular tabs thereon provide a friction fit to keep tabs 50 adjacent the side walls). As illustrated in FIG. 7, the bottom assembly is then "rolled up" by folding panel 68 along score 70 so as to be perpendicular to panel 66 which in turn is folded about score line 64 to be oriented perpendicular to intermediate panel 60. Panel 60 is similarly folded about score 62 to become perpendicular to bottom panel 54 (against which the free edge of panel 68 abuts) to form the double-walled bottom assembly which has a generally rectangular cross-section. The folded bottom assembly is then inserted into the container by folding it about score line 56, until the bottom panel 54 is generally flush with the bottom edges of the container walls.

Figure 8:
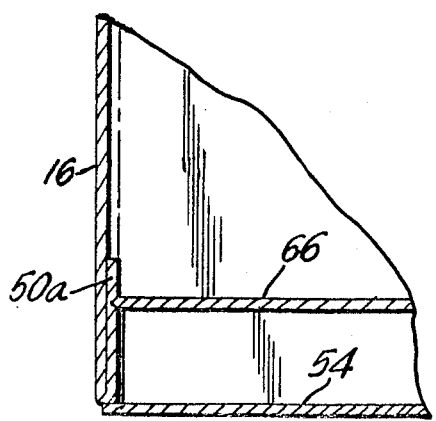
FIG. 8 is a cut-away view taken at a corner of the bottom of the container according to the present invention.

As the bottom wall assembly is being inserted into the interior container chamber, tab 72a of tongue 72 is inserted into slot 74 to help lock the bottom wall assembly in place in the container. (The front wall may have to be temporarily pulled away from the back wall in order to permit insertion of tongue 72.) To further ensure that the bottom assembly is well secured in the container, panel 66 may be proportioned so that it is at least as wide as or slightly wider than (as indicated by the dotted lines in FIG. 4) the width of the front and back walls. Thus, when the bottom wall assembly is inserted into the container, a tight friction fit will be formed between the side edges of panel 66 and the side wall tabs 50a and 50b, as shown in FIG. 8. Where panel 66 is wider than the container width, the projecting edges will tend to fold down inside the container to enhance the friction fit.

In order to assemble the top closure assembly, closure panel 22 is folded into the container along score line 38. As the panel 22 is forced into the container, it will be bent along score line 40 to permit, as indicated above, the panel to swing fully into the container interior. Tabs 42a and 42b are then folded into the container along their adjacent score lines 44 until each tab snaps behind the side edges of the first tapered edge segments (i.e., the edge portions between score 38 and offset 22a).

Figure 5:
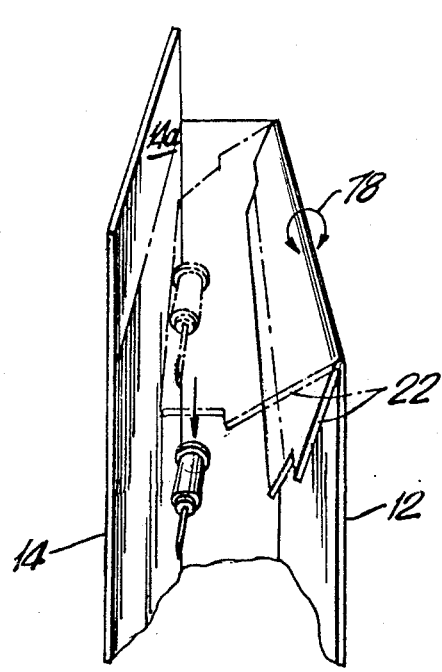
FIG. 5 is a side view, with partial cut-away, of the top portion of a container according to the present invention.

Referring then to FIG. 5, operation of the container according to the invention will be readily appreciated. When one wishes to dispose of an implement, such as the needle and syringe assembly shown in FIG. 5, the needle/syringe is simply dropped onto the downwardly sloping top panel 22, and it will come to rest in the trough formed along the inward or distal edge of panel 22 where it resides adjacent back wall panel 14. Panel 22 is then simply squeezed down toward front wall 12 (as indicatad by arrow 78), causing the needle/syringe to drop automatically into the interior of container 10 without requiring any further handling. Thus, once the disposable implement is placed in the top trough, the risk of any injury is virtually eliminated because no further handling of the implement is required. After the squeezing pressure is released, panel 22 will resiliently return to its original closed configuration, ready to receive the next discarded implement.

It will be understood that by simply folding panel 22 into the container until it clears stop edges 43a, a residual spring or biasing action is created in the hinge, causing the panel to return to its original unstressed position. Thus, closure panel 22 will automatically spring back to its closed position adjacent stop edges 43a after being opened to maintain closure of the container.

Once the container is filled, additional top panel 14a can be simply folded down over the top edges of the walls and secured in the closed configuration by, e.g, tape segments 24, as shown in FIG. 6, to form a double closure barrier. The used implements are thus safely sealed within the container for ultimate disposal (as by incineration). The double walled top and bottom assemblies, together with the doubled walled side walls (if elongated tabs 50a and 50b are used), provide extra margins of safety to prevent any implements from puncturing completely through any wall as well as prevent leakage of any residual medication or other liquids that may have collected on the used implements. All this is accomplished in an easy-to-fabricate structure which can be made from a single blank of material that can be shipped in a flattened configuration and assembled without any tape, glue or other fastener.

Figure 9:
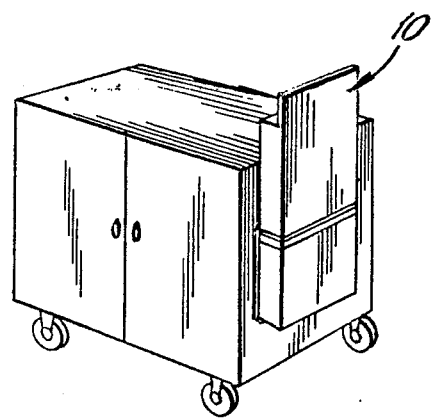
FIG. 9 is a view of an exemplary cart showing how the container according to the present invention can be conveniently and compactly supported from the cart.

Advantageously, the wall panels of container 10 are dimensioned so that the assembled container is about 20 inches tall, about 10 inches wide and about 3 inches deep. Depending on the angle at which panel 22 is to reside, the panel may be, e.g., 4 inches wide (at an angle of about 45°) or 3.5 inches wide (at an angle of about 22.5°). It will be understood that container 10 can conveniently and compactly accommodate virtually any size needle/syringe, even the large 30 cc. and 50 cc. sizes used in emergency rooms, coronary care units and intensive care units. At the same time, the container is adapted to fit conveniently on rolling service carts (as indicated in FIG. 9) while occupying a minimum of valuable space. In addition, because of the elongated "trap door" structure, the implements will naturally fall into the container in side-by-side relation so as to maximize the number of discarded implements which can be stored in the container.

It will be appreciated by those skilled in the art that the present invention in its broader aspects is not limited to the particular embodiments shown and described herein, and that variations may be made which are within the scope of the accompanying claims without departing from the principle of the invention and without sacrificing its chief advantages.

What is claimed is:

1. A container for safely storing potentially injurious implements such as scalpel blades, hypodermic needles etc., comprising a front wall panel, a back wall panel and a pair of side wall panels adapted to adjoin said front and back panels to form a box-like enclosure, a bottom wall member joined to a said wall panel at its bottom edge and adapted to engage the remaining wall panels generally at their bottom edges to form a closed-bottom container having a generally hollow interior for receiving implements to be stored, and a top closure panel hingedly joined to a said wall panel at its top edge, said top closure panel being folded into the hollow interior or said container to extend angularly inwardly into the hollow interior of said container towards an opposite wall panel to form a trough-like receiving chamber for initially receiving implements to be stored in said continer, stop means associated with said container for limiting upward angular rotation of said top closure panel to maintain said top closure panel at a predetermined angle, such that when disposal of an implement is desired, the implement can simply be released into the trough-like receiving chamber and thence caused to drop into the hollow interior of said container by pushing down on said top closure panel whereafter the implement simply falls into the container by its own weight without requiring any further handling by a person.

2. A container according to claim 1, which further includes a top tab member joined to each side wall panel along its top edge, said top tab members adapted to provide said stop means for limiting swinging travel of said top closure panel.

3. A container according to claim 2, wherein said bottom wall assembly includes:
   a bottom wall panel joined to one of said front and back wall panels along a first fold line coinciding generally with the bottom edge of said one wall panel,
   a first spacer panel joined to said bottom wall panel, with a second fold line separating said bottom wall panel and said first spacer panel, the distance between said first and second fold lines being generally equal to the width of said container, an interior bottom panel joined to said first spacer panel, with a third fold line separating said interior bottom panel from said first spacer panel, said interior bottom panel being of approximately the same width as said bottom wall panel, and a second spacer panel joined to said interior bottom panel, with a fourth fold line separating said interior bottom panel from said second spacer panel, said second spacer panel being of approximately the same width as said first spacer panel, such that when adjacent panels of said bottom wall assembly are folded by about 90 degrees, said interior bottom panel and said bottom wall panel are generally parallel.

4. A container according to claim 3, which further includes a tongue-like member formed at the bottom of the panel opposite that to which said bottom wall panel is joined, said tongue-like member including a locking tab portion, and wherein said bottom wall assembly includes a slot formed generally along a portion of said second fold line so as to receive said locking tab member for helping lock said bottom wall assembly in place.

5. A container according to claim 4, wherein at least one of said bottom wall panel and said interior bottom panel is slightly longer than the width of said container in order to form a tight friction fit at the bottom edges of said front, back and side wall panels.

6. A container according to claim 5, which further includes a bottom tab member joined at the bottom edge of each side wall panel, said bottom tab members being adapted to be folded into the interior of said container so as to extend generally parallel to said side wall panels to engage said interior bottom panel to ensure a secure friction fit.

7. A container according to claim 6, wherein said bottom tab members extend a substantial distance parallel to said side wall panels to provide a double side wall over said distance.

8. A container according to claim 1, which further includes a second tab panel extending from the top edge of the panel opposite that to which said top closure panel is joined, said said second top panel being adapted to be folded adjacent the top edges of said wall panels to provide an additional closure for said container when it is filled with discarded implements.

9. A container according to claim 8, wherein said second top member is slightly longer than the width of said container to ensure that the entire top of the container is closed by said second top panel.

10. A container according to claim 1, which is made from a single sheet of flexible material.

11. A container according to claim 3, which is made from a single sheet of flexible material.

12. A container according to claim 8, wherein said container is adapted to be shipped in a substantially flat configuration but can be assembled without requiring glue, tape, staples or other bonding or fastening means.

13. A container according to claim 9, wherein said container is adapted to be shipped in a substantially flat configuration but can be assembled without requiring glue, tape, staples or other bonding or fastening means.

14. A container for safely storing potentially injurious implements such as scalpel blades, hypodermic needles, etc., comprising a front wall panel, a back wall panel and a pair of side wall panels adjoining said front and back panels when assembled to form a box-like enclosure, a bottom wall member joined to one of said wall panels along a bottom edge thereof and residing substantially adjacent the remaining wall panels generally at their bottom edges to form a closed-bottom container having a generally hollow interior for receiving implements to be stored, and a single door-like top closure panel hingedly joined along one edge to a top edge of one of said wall panels, said top closure panel having its distal edge projecting into the hollow interior of said container to permit access into said container for implements to be stored therein when said container is assembled, said container also having a top tab member joined to a top edge portion of each of the two remaining wall panels, each said top tab member extending into said container when assembled and residing essentially adjacent a side edge of said top closure panel, each said top tab member providing stop means for limiting upward angular rotation of said top closure panel to maintain said top closure panel extending angularly inwardly into the hollow interior of said container at a generally predetermined angle to form a trough-like receiving chamber for initially receiving implements to be stored in said container, and said container including means for resiliently biasing said top closure panel generally upwardly to urge said top closure panel against said stop means of said top tab members, such that when disposal of an implement is desired, the implement can simply be released into the trough-like receiving chamber and thence caused to drop into the hollow interior of said container by pushing down on said top closure panel whereafter the implement simply falls into the container by its own weight without requiring any further handling by a person after the implement is released into the trough-like chamber and the top closure panel is urged upwardly generally until further travel is limited by said stop means to re-establish said trough-like chamber for receiving another implement for disposal.

15. A container according to claim 14, wherein the hinged joinder of said top closure panel is adapted to bias said top closure panel upwardly in self-biasing fashion, and wherein said top closure panel is joined to one of said front wall and back wall panels and said top tab members are joined to said side wall panels, such that said top closure panel extends at an acute angle into the interior of said container.

16. A container according to claim 15, wherein said top closure panel is proportioned such that the distal edge of said top closure panel resides generally closely adjacent the other of said front and back wall panels when travel of said top closure panel is limited by said stop means.

17. A container according to claim 16, wherein said top tab members act as guide means for swinging travel of said top closure panel and help substantially close the top of said container.

18. A container according to claim 14, wherein said top closure panel is tapered along its side edges from its hinged joinder to its distal edge.

19. A container according to claim 18, wherein each tapered side edge of said closure panel member includes a step-like indentation along its extent and wherein each said top tab member includes a notch-like cut-out positioned and proportioned to receive its adjacent tapered side edge of said top closure panel up to its said step-like indentation, said notch-like cut-out providing said stop means in the form of a stop edge which limits upward travel of said top closure panel.

20. An integral blank for forming a container to safely store potentially injurious implements such as scalpel blades, hypodermic needles, etc., said blank having a series of score lines to form, when assembled into said container, oppositely disposed front and back wall panels spaced apart by oppositely disposed side wall panels to define a box-like enclosure with a bottom wall member joined to one of said wall panels along its bottom edge and a top panel member joined to a said wall panel at its top edge a pair of top tab members joined along the wall panels adjacent the wall panel to which said top closure panel is joined, each said top tab member providing stop means for limiting angularly upward rotation of said top closure panel for maintaining said top closure panel projecting at an angle into said container when assembled, such that when said blank is assembled into said container, said top tab members and said top panel are folded into the container by more than 90° to project into the container with said top panel residing between said top tab members and projecting angularly inwardly towards the wall panel opposite the wall panel to which said top closure panel is attached to form a trough-like recess for initially receiving implements to be stored in said container, said top panel being resiliently biased to its closed configuration substantially by reason of the more than 90° folding.

* * * * *